(12) United States Patent
Meng et al.

(10) Patent No.: US 10,786,241 B2
(45) Date of Patent: Sep. 29, 2020

(54) KNOT-TYING DEVICE AND KNOT-TYING SYSTEM WITH KNOT-TYING DEVICE

(71) Applicant: BEIJING MED ZENITH MEDICAL SCIENTIFIC CO., LTD., Beijing (CN)

(72) Inventors: Jian Meng, Beijing (CN); Baoqi Xie, Beijing (CN); Zhiwei Ma, Beijing (CN); Zhiwu Zhang, Beijing (CN); Shengbo Dou, Beijing (CN); Xiaojun Zhou, Beijing (CN); Kang Wu, Beijing (CN); Danian Ke, Beijing (CN)

(73) Assignee: BEIJING MED ZENITH MEDICAL SCIENTIFIC CO., LTD., Beijing (CN)

( * ) Notice: Subject to any disclaimer, the term of this patent is extended or adjusted under 35 U.S.C. 154(b) by 191 days.

(21) Appl. No.: 16/305,896

(22) PCT Filed: Oct. 31, 2016

(86) PCT No.: PCT/CN2016/104009
§ 371 (c)(1),
(2) Date: Nov. 30, 2018

(87) PCT Pub. No.: WO2017/206431
PCT Pub. Date: Dec. 7, 2017

(65) Prior Publication Data
US 2019/0374216 A1  Dec. 12, 2019

(30) Foreign Application Priority Data

Jun. 1, 2016 (CN) .......................... 2016 1 0384302

(51) Int. Cl.
*A61B 17/04* (2006.01)
(52) U.S. Cl.
CPC ...... *A61B 17/0469* (2013.01); *A61B 17/0467* (2013.01); *A61B 2017/0474* (2013.01)

(58) Field of Classification Search
CPC ............ A61B 17/0469; A61B 17/0467; A61B 2017/0474; A61B 2017/2946; A61B 17/2909; A61B 17/285
See application file for complete search history.

(56) References Cited

U.S. PATENT DOCUMENTS

| 5,643,289 A | 7/1997 | Sauer et al. |
| 8,702,730 B2 | 4/2014 | Shriver |
| 2002/0087178 A1* | 7/2002 | Nobles ............... A61B 17/0467 606/167 |

(Continued)

FOREIGN PATENT DOCUMENTS

| CN | 202892020 U | 4/2013 |
| CN | 204016382 U | 12/2014 |

(Continued)

OTHER PUBLICATIONS

EP first Search Report dated Dec. 16, 2019 re: Application No. 16903813.0, pp. 1-7.

(Continued)

*Primary Examiner* — Katrina M Stransky
(74) *Attorney, Agent, or Firm* — Gang Yu

(57) ABSTRACT

The present disclosure discloses a knot-tying device and a knot-tying system with the knot-tying device. The knot-tying device comprises a shear knife provided at a front end of a driving rod. Hilts of the shear knife (18) are opened by an elastic member, and the hilts are pressed by the driving rod to close and cut a suture. The shear knife is used as a substitute for a cutter in the related art, and is driven to close by the driving rod so as to realize a shearing function. When the suture is cut off by the shear knife, a requirement for sharpness of blades are greatly reduced, and the blades are able to be realized by a common processing method, thereby greatly reducing cost while ensuring reliability. In addition, abrasion on the blades from the suture is reduced, thereby greatly prolonging the service life of the product.

13 Claims, 3 Drawing Sheets

(56) References Cited

U.S. PATENT DOCUMENTS

| | | | |
|---|---|---|---|
| 2003/0120287 A1* | 6/2003 | Gross | A61B 17/0469 606/148 |
| 2003/0181926 A1* | 9/2003 | Dana | A61B 17/0485 606/148 |
| 2003/0204205 A1 | 10/2003 | Sauer et al. | |
| 2004/0254598 A1* | 12/2004 | Schumacher | A61B 17/0467 606/170 |
| 2007/0106310 A1* | 5/2007 | Goldin | A61B 17/0467 606/148 |
| 2009/0082797 A1* | 3/2009 | Fung | A61B 17/0467 606/170 |
| 2014/0005689 A1* | 1/2014 | Griffiths | A61B 17/0467 606/138 |
| 2014/0276979 A1* | 9/2014 | Sauer | A61B 17/0469 606/144 |
| 2015/0088163 A1* | 3/2015 | George | A61B 17/0467 606/138 |
| 2016/0007986 A1* | 1/2016 | Sauer | A61B 17/0469 606/139 |
| 2016/0199056 A1* | 7/2016 | Harrison | A61B 17/0467 606/138 |

FOREIGN PATENT DOCUMENTS

| | | |
|---|---|---|
| CN | 204723113 U | 10/2015 |
| CN | 205814366 U | 12/2016 |
| EP | 1832236 A2 | 12/2007 |
| WO | 2004024006 A1 | 3/2004 |
| WO | 2015151627 A1 | 10/2015 |
| WO | 2016007973 A2 | 1/2016 |

OTHER PUBLICATIONS

International Search Report for PCT application No. PCT/CN2016/104009 filed on Oct. 31, 2016, dated Feb. 22, 2017.

* cited by examiner

KNOT-TYING DEVICE AND KNOT-TYING SYSTEM WITH KNOT-TYING DEVICE

CROSS REFERENCE TO RELATED APPLICATIONS

The present application claims benefit of Chinese patent application No. 201610384302.2, filed on Jun. 1, 2016, the contents of which are hereby incorporated by reference in its entirety.

TECHNICAL FIELD

The present disclosure relates to the technical field of surgical instruments, and particularly to a knot-tying device and a knot-tying system with the knot-tying device.

BACKGROUND

Various disadvantages exist when knot-tying at a deep part is completed by virtue of a traditional manual winding manner. For example, time and labor is able to consumed, a suture needs to be manually sheared off in repeated times by a scissor, knot-tying effect and success rate over-depend on proficiency of an operator, and the like.

In order to solve the above problems, a patent with a patent number of CN202892020U discloses a minimally invasive knot-tying system. The minimally invasive knot-tying system is capable of performing suturing and knot-tying in a minimally invasive environment, and is mainly applicable to deep suturing of cardiac valves subjected to minimally invasive replacement and all repaired intrathoacic soft tissues. The minimally invasive knot-tying system is simple in operation, capable of simultaneously completing a suture-cutting operation by virtue of one-time knot-tying, high in knot-tying success rate, solid and reliable in knot-tying and wide in knot-tying environment, may almost perform knot-tying in any minimally invasive environment, and provides a convenient, high-efficiency and reliable knot-tying tool for a surgeon.

The minimally invasive knot-tying system in the present disclosure includes a knot-tying device shown in FIG. 1 and a guide thread ring shown in FIG. 2. The knot-tying device includes a handle, a trigger 1, a driving rod 6, a sleeve 7, a cutter 8 and a punching shear wedge 12. The handle and the trigger 1 are connected by virtue of a first hinge piece 4 and a tension spring 3, and a tail end of the driving rod 6 and the trigger 1 are connected by virtue of a second hinged piece 5. In addition, the guide thread ring includes a traction hook 14, a closing nail 15 and a guide thread 16.

In an operating process, both ends of a suture are led in from a first threading hole 9 and led out of a second threading hole 10 by using the guide thread ring, and the closing nail 15 is arranged in the first threading hole 9. On such a basis, the trigger 1 is pressed, and the driving rod 6 is driven to move forwards. Along with a forward movement of the driving rod 6, a punching tongue 11 on the driving rod 6 acts on the punching shear wedge 12 and further acts on the closing nail 15 so as to complete knot-tying of the suture, and the cutter 8 moves forwards to complete cutting of the suture. The cutter 8 is fixed in a cutter clamping groove 13.

A cutting principle of the cutter 8 is further with reference to FIG. 3. Defects existing in such a cutting manner are as follows: a cutter of general sharpness cannot be cut off the suture in a normal circumstance, the cutter is required to have higher sharpness, the suture cutting is difficult to realize in a conventional production technology, and cost is very high. Moreover, since the cutter is for cutting off the suture, blades of a cutter made of a general material are easily damaged to cause that the suture cannot be cut off and an operation cannot be completed.

SUMMARY

(I) Technical Problems to be Solved

A purpose of some embodiments of the present disclosure is to provide a knot-tying device and a knot-tying system having the knot-tying device, for solving problems in a knot-tying device in the related art that a requirement on sharpness of a cutter is too high, and once blades of the cutter are damaged, surgical instruments are adverse even fail and then an operation is delayed.

(II) Technical Solution

In order to solve the technical problems above, an embodiment of the present disclosure provides a knot-tying device. The knot-tying device includes a handle, a trigger connected with the handle by a rotating shaft, a sleeve fixed on the handle, a driving rod that is connected with the trigger and arranged in the sleeve and reciprocates in the sleeve, and a punching shear wedge that is provided at a front end of the sleeve and is able to open and close, so that the punching shear wedge, when being pressed by the driving rod, closes to achieve a pressing effect, the knot-tying device further includes a shear knife provided at a front end of the driving rod. Hilts of the shear knife are propped open by an elastic member, the hilts, when being pressed by the driving rod, close to enable the shear knife to cut a suture.

In an exemplary embodiment, the hilts include a first handle portion and a second handle portion hinged with each other, and the elastic member is arranged between the first handle portion and the second handle portion.

In an exemplary embodiment, the driving rod includes a U-shaped groove, wherein the U-shaped groove is used for pressing the first handle portion and the second handle portion in opposite directions.

In an exemplary embodiment, a first stress arm is provided at an end of the first handle portion, a second stress arm is provided at an end of the second handle portion, and the first stress arm and the second stress arm gradually draw close to each other along a direction towards the U-shaped groove.

In an exemplary embodiment, the first handle portion and the second handle portion are hinged by a rivet, and one end of the rivet is fixedly inserted into the punching shear wedge.

In an exemplary embodiment, the elastic member is a compressed spring.

In an exemplary embodiment, the punching shear wedge is a retractable metal clip composed of two blades of which roots are connected, wherein one blade of the two blades includes a punching surface, the other blade of the two blades includes a cutting surface, and the blade including the cutting surface is contacted with an inner wall of the sleeve.

The present disclosure further provides a minimally invasive knot-tying system which includes the knot-tying device and further includes a guide thread ring.

(III) Beneficial Effects

The solution of the present disclosure has beneficial effects as follows: the knot-tying device in the present disclosure includes a handle, a trigger connected with the handle by a rotating shaft, a sleeve fixed on the handle, a driving rod that is connected with the trigger and arranged in the sleeve and reciprocates in the sleeve, and a punching shear wedge that is provided at a front end of the sleeve and is able to open and close, so that the punching shear wedge, when being pressed by the driving rod, closes to achieve a pressing effect, and further includes a shear knife provided at a front end of the driving rod. Hilts of the shear knife are propped open by an elastic member, the hilts, when being pressed by the driving rod, close to enable the shear knife to cut a suture. According to the knot-tying device in the solution, the shear knife is used as a substitute for a cutter in the related art, and is driven to close by the driving rod so as to realize a shearing function. Apparently, when the suture is cut off by the shear knife, the requirement for sharpness of blades are greatly reduced, and the blades are able to be realized by common processing method, thereby greatly reducing cost while ensuring reliability. In addition, abrasion on the blades from the suture is reduced in the solution, thereby greatly prolonging the service life of the product and being able to realize a suture-cutting function in a faster and better manner after knot-tying.

BRIEF DESCRIPTION OF THE DRAWINGS

In order to clearly describe technical schemes in embodiments of the present disclosure or in a related art, drawings needing to be used in description of the embodiments or the related art are briefly introduced below. Apparently, the drawings in the description below are some embodiments of the present disclosure only. On premise of not making creative work, those ordinary skilled in the art may obtain other drawings according to these drawings.

Figure 1:
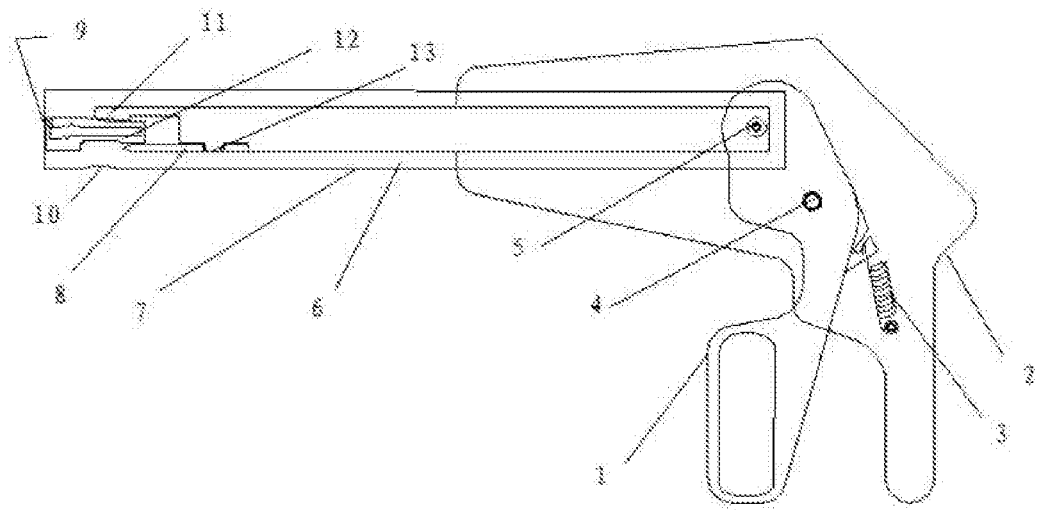
FIG. 1 schematically shows a structure diagram of a knot-tying device in background.
Figure 2:
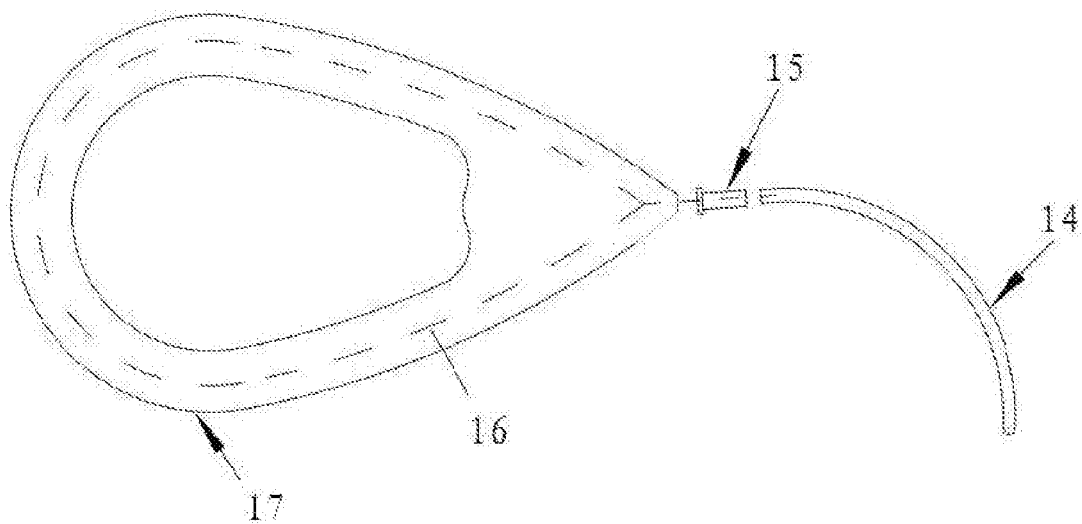
FIG. 2 schematically shows a structure diagram of a guide thread ring in background.
Figure 3:
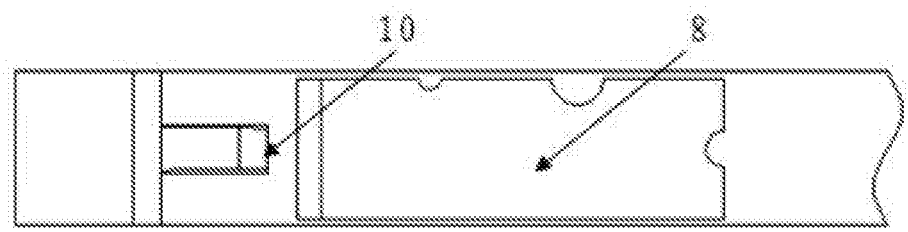
FIG. 3 shows a schematic diagram of a shearing principle of a suture in a knot-tying device in background.

In the figures: 1, trigger; 2, handle; 3, tension spring; 4, first hinged piece; 5, second hinged piece; 6 driving rod; 7, sleeve; 8, cutter; 9, first threading hole; 10, second threading hole; 11, punching tongue; 12, punching shear wedge; 13, cutter clamping groove; 14, traction hook; 15, closing nail; 16, guide thread; 17, guide thread rack; 18, shear knife; 181, first stress arm; 182, second stress arm; 19, compressed spring; 20, rivet; 21, U-shaped groove.

DETAILED DESCRIPTION OF THE EMBODIMENTS

The implementation manners of the present disclosure will be further described in detail below with reference to the accompanying drawings and embodiments. The following embodiments are used to illustrate the present disclosure, but are not used to limit the scope of the present disclosure.

In the description of the present disclosure, it should be noted that, the orientation or positional relationship indicated by the terms "longitudinal", "transverse", "up", "down", "front", "rear", "left", "right", "vertical", "horizontal", "top", "bottom", "inner", "outer", etc. is the orientation or positional relationship shown in the drawings, which is merely for the convenience of describing the present disclosure and simplifying the description, and does not indicate or imply that the referred device or element must have a specific orientation and must be constructed and operated in a specific orientation, and thus it cannot be construed as a limitation of the present disclosure. Moreover, the terms "first," "second," "third," etc., are used for descriptive purposes merely, and cannot be construed as indicating or implying relative importance.

In the description of the present disclosure, unless otherwise specified and limited, it should be noted that terms "mutual connection" and "connection" should be generally understood. For example, the term is able to fixed connection, or detachable connection or integrated connection, is able to mechanical connection or electrical connection, is able to direct connection, is able to indirect connection through an intermediate, or is able to internal communication between two elements. A person of ordinary skill in the art may understand specific meanings of the above terms in the present disclosure according to specific situations.

Without loss of generality, the embodiment is described by taking a minimally invasive knot-tying field as an example. It should be noted that, in addition to a minimally invasive technical field, the knot-tying device and knot-tying system in the embodiment is able to further apply to any field with knot-tying needs.

Figure 4:
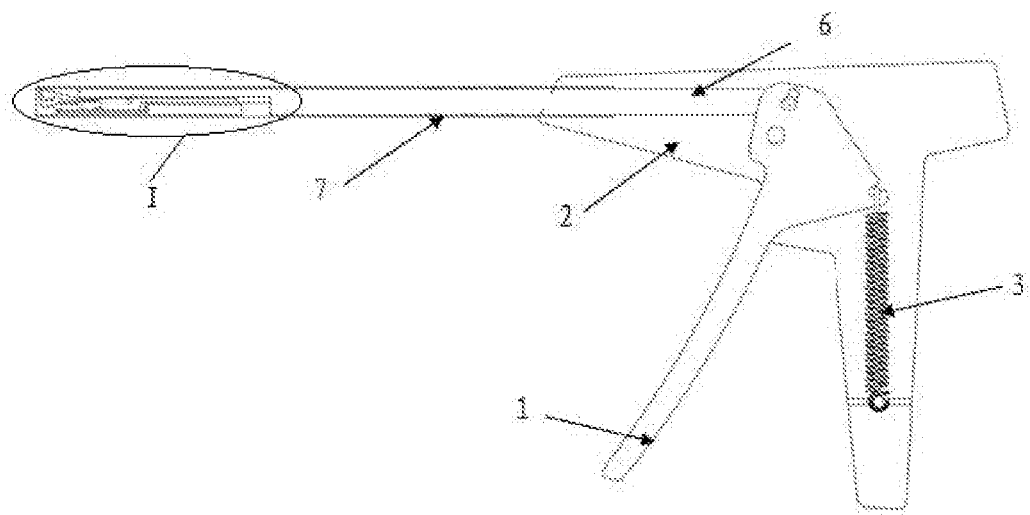
FIG. 4 schematically shows a structure diagram of a knot-tying device in the embodiment.

With reference to FIG. 4, the knot-tying device in an embodiment includes a handle, a trigger 1 connected with the handle by a rotating shaft, a sleeve 7 fixed on the handle, a driving rod 6 that is connected with the trigger 1 and arranged in the sleeve 7 and reciprocates in the sleeve 7, and a punching shear wedge (non-marked in the figure) that is provided at a front end of the sleeve 7 and is able to open and close to be pressed by the driving rod 6 to close so as to achieve a pressing effect. On the basis, a difference between the knot-tying device in the embodiment and a knot-tying device in the related art is a difference of shear structures of a suture, that is, a part I in FIG. 4. The handle and the trigger 1 are connected by a tension spring 3.

Figure 5:
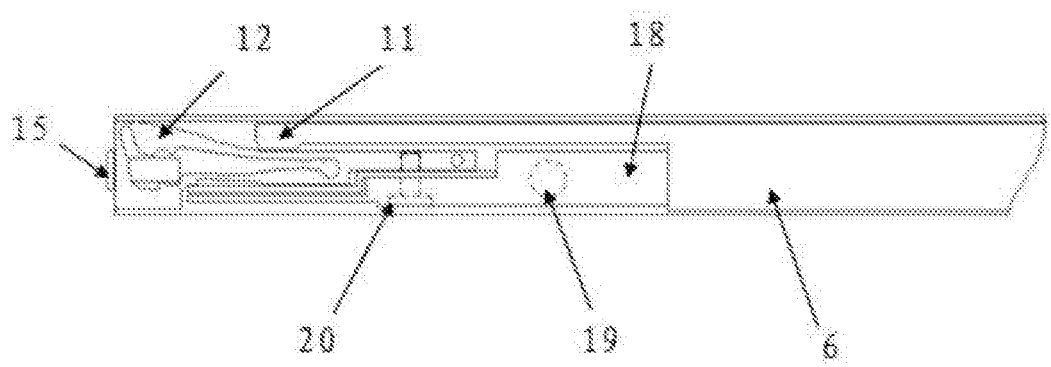
FIG. 5 shows a partially enlarged schematic diagram of FIG. 4.

As shown in FIG. 5, the knot-tying device in the embodiment further includes a shear knife 18 provided at a front end of the driving rod 6. Hilts of the shear knife 18 is propped opened by an elastic member, so that a cutting head part of the shear knife 18 keeps opening, thereby ensuring a normal threading operation. Along with a forward movement of the driving rod 6, the hilts, when being pressed by the driving rod 6, close to enable the shear knife 18 to cut a suture.

According to the knot-tying device in the embodiment, the shear knife 18 is used as a substitute for a cutter 8 in the related art, and is driven to close by the driving rod 6 so as to realize a shearing function. Apparently, when the suture is cut off by the shear knife, the requirement for sharpness of blades are greatly reduced, and the blades are able to be realized by common processing method, thereby greatly reducing cost while ensuring reliability. In addition, abrasion on the blades from the suture is reduced in the solution, thereby greatly prolonging the service life of the product and being able to realize a suture-cutting function in a faster and better manner after knot-tying.

Figure 6:
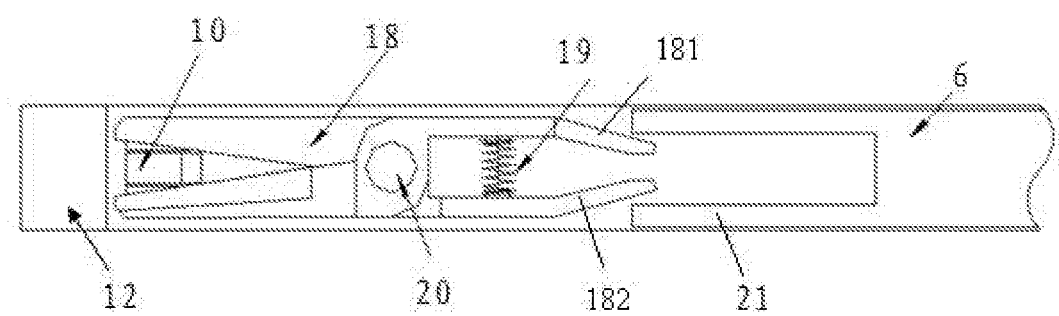
FIG. 6 shows a schematic diagram of a shearing principle of a suture in a knot-tying device in the embodiment.

As shown in FIG. 6, the shear knife 18 in the embodiment includes a first shear body and a second shear body hinged with each other, and the first shear body and the second shear body respectively include a cutting head part and a handle part. Wherein the first shear body includes a first handle portion, the second shear body includes a second handle portion, and the first handle portion and the second handle portion are combined to form the hilts of the shear knife 18. The elastic member in the embodiment is arranged between the first handle portion and the second handle portion, so that the shear knife 18 is keep in an opening state, and then a traction hook 14, a guide thread 16 and the suture may smoothly penetrate through a gap of the cutting head part of the shear knife 18.

The elastic member may adopt a compressed spring 19 in the embodiment. Certainly, as long as closing and opening functions of the hilts are able to complete when the driving rod 6 moves forwards and backwards, any elastic member disclosed in any of other related arts should be included in a protection scope of the present disclosure.

In addition, in order to close the hilts and finally complete cutting of the suture, the driving rod 6 in the embodiment includes a U-shaped groove 21. While moving towards the hilts of the shear knife 18, the U-shaped groove 21 may press the first handle portion and the second handle portion of the shear knife 18 in opposite directions.

On the basis, with further reference to FIG. 6, a first stress arm 181 is provided at an end of the first handle portion, a second stress arm 182 is provided at an end of the second handle portion, and the first stress arm 181 and the second stress arm 182 gradually draw close to each other along a direction towards the U-shaped groove 21. When the U-shaped groove 21 moves towards a direction in which the handle is positioned, the first handle portion and the second handle portion of the shear knife enter the U-shaped groove 21 and are pressed by side walls of the U-shaped groove 21, the compressed spring 19 is compressed, and the first stress arm 181 and the second stress arm 182 are driven to draw close to each other, thereby achieving an effect of closing and cutting of the suture.

Certainly, structures of the driving rod 6 and the hilts are not limited by the drawings, as long as the driving rod 6 may drive the hilts to close, and the shear knife 18 realizes cutting of the suture.

Since the first shear body and the second shear body are hinged, that is, the first handle portion and the second handle portion are hinged, and a hinged piece is preferably but does not have to be a rivet 20, please refer to FIG. 6. Moreover, in combination with FIG. 5, one end of the rivet 20 is fixedly inserted into the punching shear wedge 12, thereby ensuring firm positioning of the shear knife 18.

Further, the punching shear wedge 12 is a retractable metal clip composed of two blades of which roots are connected, wherein one blade of the two blades includes a punching surface, and the other blade of the two blades includes a cutting surface. In the embodiment, in order to ensure fixation of the punching shear wedge 12 in the sleeve, with further reference to FIG. 5, the blade including the cutting surface in the punching shear wedge 12 is contacted with an inner wall of the sleeve, that is, a lower blade in FIG. 5 is contacted with the inner wall of the sleeve.

On the basis, the embodiment further provides a minimally invasive knot-tying system including the knot-tying device above and a guide thread ring. In addition, the guide thread ring includes the traction hook 14, a closing nail 15 and the guide thread 16. Along with a forward movement of the driving rod 6, a punching tongue 11 on the driving rod 6 acts on the punching shear wedge 12 and further acts on the closing nail 15 so as to complete knot-tying of the suture, and the cutter 8 moves forwards to complete cutting of the suture.

The embodiments above are only for illustrating the present disclosure, rather than a limitation of the present disclosure. Although the present disclosure is described in detail with reference to the embodiments, those ordinary skilled in the art should understand that, on premise of deviating from the spirit and scope of the technical schemes in the present disclosure, various combinations, modifications or equivalent replacements of the technical schemes of the present disclosure should be included in the scope of claims of the present disclosure.

INDUSTRIAL APPLICABILITY

The present disclosure relates to the technical field of surgical instruments and provides a knot-tying device and a knot-tying system having the knot-tying device. The knot-tying device includes a shear knife provided at a front end of a driving rod. Hilts of the shear knife are propped open by an elastic member, the hilts, when being pressed by the driving rod, close to enable the shear knife to cut a suture. According to the knot-tying device in the solution, the shear knife is used as a substitute for a cutter in the related art, and is driven to close by the driving rod so as to realize a shearing function. Apparently, when the suture is cut off by the shear knife, the requirement for sharpness of blades are greatly reduced, and the blades are able to be realized by common processing method, thereby greatly reducing cost while ensuring reliability. In addition, abrasion on the blades from the suture is reduced in the solution, thereby greatly prolonging the service life of the product and being able to realize a suture-cutting function in a faster and better manner after knot-tying. The knot-tying device and the knot-tying system having the knot-tying device are low in cost, long in service life, high in knot-tying efficiency and favorable for popularization, thereby achieving extremely high practicality.

What is claimed is:

1. A knot-tying device, comprising: a handle, a trigger connected with the handle by a rotating shaft, a sleeve fixed on the handle, a driving rod that is connected with the trigger and arranged in the sleeve and reciprocates in the sleeve, and a punching shear wedge that is provided at a front end of the sleeve and is able to open and, close, so that the punching shear wedge, when being pressed by the driving rod, closes to achieve a pressing effect, wherein the knot-tying device further comprises a shear knife provided at a front end of the driving rod, hilts of the shear knife are propped open by an elastic member, the hilts, when being pressed by the driving rod, close to enable the shear knife to cut a suture.

2. The knot-tying device as claimed in claim 1, wherein the hilts comprise a first handle portion and a second handle portion hinged with each other, and the elastic member is arranged between the first handle portion and the second handle portion.

3. The knot-tying device as claimed in claim 2, wherein the punching shear wedge is a retractable metal clip composed of two blades of which roots are connected, one blade of the two blades comprises a punching surface, the other blade of the two blades comprises a cutting surface, and the blade comprising the cutting surface is contacted with an inner wall of the sleeve.

4. The knot-tying device as claimed in claim 2, wherein the driving rod comprises a U-shaped groove, and the U-shaped groove is used for pressing the first handle portion and the second handle portion in opposite directions.

5. The knot-tying device as claimed in claim 4, wherein the punching shear wedge is a retractable metal clip composed of two blades of which roots are connected, one blade of the two blades comprises a punching surface, the other blade of the two blades comprises a cutting surface, and the blade comprising the cutting surface is contacted with an inner wall of the sleeve.

6. The knot-tying device as claimed in claim 4, wherein a first stress arm is provided at an end of the first handle portion, a second stress arm is provided at an end of the second handle portion, and the first stress arm and the second stress arm gradually draw close to each other along a direction towards the U-shaped groove.

7. The knot-tying device as claimed in claim 6, wherein the punching shear wedge is a retractable metal clip composed of two blades of which roots are connected, one blade of the two blades comprises a punching surface, the other blade of the two blades comprises a cutting surface, and the blade comprising the cutting surface is contacted with an inner wall of the sleeve.

8. The knot-tying device as claimed in claim 2, wherein the first handle portion and the second handle portion are hinged by a rivet, and one end of the rivet is fixedly inserted into the punching shear wedge.

9. The knot-tying device as claimed in claim 8, wherein the punching shear wedge is a retractable metal clip composed of two blades of which roots are connected, one blade of the two blades comprises a punching surface, the other blade of the two blades comprises a cutting surface, and the blade comprising the cutting surface is contacted with an inner wall of the sleeve.

10. The knot-tying device as claimed in claim 1, wherein the elastic member is a compressed spring.

11. The knot-tying device as claimed in claim 4, wherein the punching shear wedge is a retractable metal clip composed of two blades of which roots are connected, one blade of the two blades comprises a punching surface, the other blade of the two blades comprises a cutting surface, and the blade comprising the cutting surface is contacted with an inner wall of the sleeve.

12. The knot-tying device as claimed in claim 1, wherein the punching shear wedge is a retractable metal clip composed of two blades of which roots are connected, one blade of the two blades comprises a punching surface, the other blade of the two blades comprises a cutting surface, and the blade comprising the cutting surface is contacted with an inner wall of the sleeve.

13. A minimally invasive knot-tying system, wherein the minimally invasive knot-tying system comprises the knot-tying device as claimed in claim 1, and the minimally invasive knot-tying system further comprises a guide thread ring.

\* \* \* \* \*